US006704598B2

(12) United States Patent
Ding et al.

(10) Patent No.: US 6,704,598 B2
(45) Date of Patent: Mar. 9, 2004

(54) CARDIAC RHYTHM MANAGEMENT SYSTEM SELECTING BETWEEN MULTIPLE SAME-CHAMBER ELECTRODES FOR DELIVERING CARDIAC THERAPY

(75) Inventors: Jiang Ding, Maplewood, MN (US); Julio C. Spinelli, Shoreview, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 72 days.

(21) Appl. No.: 09/862,181

(22) Filed: May 23, 2001

(65) Prior Publication Data

US 2002/0177879 A1 Nov. 28, 2002

(51) Int. Cl.$^7$ .............................................. A61N 1/365
(52) U.S. Cl. ........................................................ 607/9
(58) Field of Search .............................. 607/4, 5, 9, 14

(56) References Cited

U.S. PATENT DOCUMENTS

| | | | | |
|---|---|---|---|---|
| 5,181,511 A | * | 1/1993 | Nickolls et al. | 607/14 |
| 5,995,870 A | | 11/1999 | Cazeau et al. | 607/9 |
| 6,076,013 A | | 6/2000 | Brennan et al. | 607/2 |
| 2002/0082656 A1 | * | 6/2002 | Stahmann et al. | 607/9 |

FOREIGN PATENT DOCUMENTS

| WO | WO-99/58191 | 11/1999 | A61N/1/368 |
|---|---|---|---|

OTHER PUBLICATIONS

Alonso, C., et al., "ECG Predictive Factors of Positive Response to Multisite Biventricular Pacing in Advanced Heart Failure", *PACE 22*, NASPE Abstract No. 232, p. 758, (Apr. 1999).

Alonso, C., et al., "Influence of Left and Right Ventricular Pacing Sites on QRS Characteristics during Biventricular Pacing in Advanced Heart Failure", *PACE, 22*, NASPE Abstract No. 644, p. 861, (Apr. 1999).

Alonso, C., et al., "Intravascular Extraction of Leads Chronically Implanted Into the Cardiac Veins For Permanent Left Ventricular Pacing", *PACE, 23*, NASPE Abstract No. 35, p. 561, (Apr. 2000).

Alonso, C., et al., "Long–Term Performances of Transvenous Left Ventricular Leads: A 5 Years Experience", *PACE, 23*, NASPE Abstract No. 233, p. 611, (Apr. 2000).

Auricchio, A., et al., "Acute Hemodynamic Improvement by Pacing in Patients with Severe Congestive Heart Failure", *PACE, 20*, pp. 313–324, (Feb. 1997).

Auricchio, A., et al., "Clinical and Objective Improvements in Sever Congestive Heart Failure Patients Using Univentricular or Biventricular Pacing: Preliminary Results of a Randomized Prospective Study", *JACC*, Abstract No. 1015–30, p. 31A, (Feb. 1998).

Auricchio, A., et al., "Effect of Pacing Chamber and Atrioventricular Delay on Acute Systolic Function of Paced Patients With Congestive Heart Failure", *Circulation, 99*, pp. 2993–3001, (1999).

(List continued on next page.)

*Primary Examiner*—George R. Evanisko
(74) *Attorney, Agent, or Firm*—Schwegman, Lundberg, Woessner & Kluth, P.A.

(57) ABSTRACT

A cardiac rhythm management system selects one of multiple electrodes associated with a particular heart chamber based on a relative timing between detection of a depolarization fiducial point at the multiple electrodes, or based on a delay between detection of a depolarization fiducial point at the multiple electrodes and detection of a reference depolarization fiducial point at another electrode associated with the same or a different heart chamber. Subsequent contraction-evoking stimulation therapy is delivered from the selected electrode.

18 Claims, 7 Drawing Sheets

OTHER PUBLICATIONS

Auricchio, A., et al., "The Pacing Therapies for Congestive Heart Failure (PATH–CHF) Study: Rationale, Design, and Endpoints of a Prospective Radomized Multicenter Study", *Am. J. Cardiol., 83 (5B)*, pp. 130D–135D, (Mar. 1999).

Blanc, J., et al., "Evaluation of Different Ventricular Pacing Sites in Patients With Severe Heart Failure", *Circulation 96 (10)*, pp. 3273–3277, (1997).

Cazeau, S., et al., "4-year experience of Biventricular pacing for congestive heart failure", *PACE, 21*, NASPE Abstract No. 8, p. 791, (Apr. 1998).

Cazeau, S., et al., "Acute Electromechanical comparison of biventricular versus conventional DDD Stimulation in congestive heart failure patients", *PACE, 21*, NASPE Abstract No. 744, p. 975, (Apr. 1998).

Cazeau, S., et al., "Biventricular pacing decreases interventricular but not intraventricular asynchrony in multisite— paced patients for congestive heart failure", *PACE, 21*, NASPE Abstract No. 9, p. 792, (Apr. 1998).

Cazeau, S., et al., "Heart Failure: Acute hemodynamic improvement provided by multisite biventricular pacing", *JACC—Abstracts*, Abstract No. 935–70, p. 111A, (Feb. 1997).

Cazeau, S., et al., "Overlap between systole and diastole in congestive heart failure patients candidates for multisite biventricular pacing", *PACE, 21*, NASPE Abstract No. 743, p. 975, (Apr. 1998).

Daubert, C., et al., "Outcome of Patients Chronically Implanted with Biventricular Pacing Systems, for Endstage Congestive Heart Failure", *PACE, 20, NASPE Abstracts, Part II*, Abstract No. 215, p. 1103, (Apr. 1997).

Daubert, C., et al., "Use of Specifically Designed Coronary Sinus Leads for Permanent Left Ventricular Pacing: Preliminary Experience", *PACE, vol. 20, NASPE Abstracts, Part II*, Abstract No. 17, p. 1054, (Apr. 1997).

Daubert, J., et al., "Clinical Effects of Biventricular Pacing in Patients with Severe Heart Failure and Normal Sinus Rhythm: Results from the Multisite Stimulation in Cardimyopathy–MUSTIC—Group I", *Circulation, Suppl. II, 102 (18)*, Abstract No. 3353, p. II–694, (Oct. 2000).

Daubert, J., et al., "Clinical Effects of Biventricular Pacing in Patients with Severe Heart Failure and Normal Sinus Rhythm: Results from the Multisite Stimulation in Cardiomyopathy–MUSTIC—Group I", *Circulation, Suppl. II, 102 (18)*, Abstract No. 3354, p. II–694, (Oct. 2000).

Daubert, J.C., et al., "Permanent Biventricular Pacing by a Transvenous Approach", *JACC*, Abstract No. 1045–110, p. 431A, (Feb. 1997).

Daubert, L.C., et al., "Permanent Left Ventricular Pacing With Transvenous Leads Inserted Into the Coronary Veins", *PACE, 21*, p. 239–245, (Jan. 1998).

Ding, J., et al., "Can Intraventricular Electromechanical Synchrony Account for the Increase in LV +dp/dt When Pacing Heart Failure Patients at Left Ventricular Lateral Wall?", *Abstracts From the 71st Scientific Sessions*, Abstract No. 1582, p. I–303, (1998).

France, R., et al., "Clinical Effects of Biventricular Pacing in Patients with Severe Heart Failure and Chronic Atrial Fibrillation: Results from the Multisite Stimulation in Cardiomyopahty–MUSTIC Study—Group II", *Clinical Science, Abstracts from Scientific Sessions*, Abstract No. 3349, p. II–693, (2000).

Gras, D., et al., "First experience with coronary sinus leads used for permanent Left Ventricular pacing", *PACE, 21*, NASPE Abstract No. 141, p. 825, (Apr. 1998).

Gras, D., et al., "Long Term Results of Cardiac Resynchronization for Heart Failure Patients: The InSync Clinical Trial", *Abstracts from the 72nd Scientific Sessions*, Abstract No. 2714, p. I–515, (2000).

Gras, D., et al., "Multisite Pacing as a Supplemental Treatment of Congestive Heart Failure: Preliminary Results of the Medtronic Inc. InSync Study", *PACE, 21*, pp. 2249–2255, (Nov. 1998).

Gras, D., et al., "Permanent Cardiac Resynchronization after Sustained Clinical Improvement in Heart Failure Patients: The InSync Trial", *PACE, 22*, NASPE Abstract No. 803, p. 901, (Apr. 1999).

Kass, D.A., et al., "Improved Left Ventricular Mechanics From Acute VDD Pacing in Patients With Dilated Cardiomyopathy and Ventricular Conduction Delay", *Circulation, 99*, pp. 1567–1573, (1999).

Leclercq, C., et al., "Comparative Effects of Permanent Biventricular Pacing in Class III and Class IV Patients", *PACE, 21*, NASPE Abstract No. 488, p. 911, (Apr. 1998).

Leclercq, C., et al., "Does the Etiology of Chronic Left Ventricular Dysfunction Influence the Long Term Effects of Biventricular Pacing in Patients with Severe Heart Failure?", *PACE, 21*, NASPE Abstract No. 569, p. 932, (Apr. 1998).

Leclercq, C., et al., "Long Term Results of Permanent Biventricular Pacing in patients with Advanced Heart Failure: Comparison of Patient with Stable Sinus Rhythm and Chronic Atrial Fibrillation", *PACE, 23*, NASPE Abstract No. 329, p. 635, (Apr. 2000).

Leclercq, C., et al., "Multisite Biventricular Pacing in Advanced Heart Failure, Current Status of the French Pilot Study", *PACE, 22*, NASPE Abstract No. 134, p. 733, (Apr. 1999).

Yu, Y., et al., "Experimental Validation of Pulse Contour Methods for Estimating Stroke Volume at Pacing Onset", *Proceedings of the 20th Annual International Conference of the IEEE Engineering in Medicine and Biology Society, 20 (1)*, pp. 401–404, (1998).

* cited by examiner

CARDIAC RHYTHM MANAGEMENT SYSTEM SELECTING BETWEEN MULTIPLE SAME-CHAMBER ELECTRODES FOR DELIVERING CARDIAC THERAPY

TECHNICAL FIELD

The present system relates generally to cardiac rhythm management systems and particularly, but not by way of limitation, to such a system selecting between multiple same-chamber electrodes for delivering cardiac therapy.

BACKGROUND

When functioning properly, the human heart maintains its own intrinsic rhythm based on physiologically-generated electrical impulses. It is capable of pumping adequate blood throughout the body's circulatory system. Each complete cycle of drawing blood into the heart and then expelling it is referred to as a cardiac cycle.

However, some people have abnormal cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by physicians treating cardiovascular patients is the treatment of congestive heart failure (also referred to as "CHF"). Congestive heart failure, which can result from long-term hypertension, is a condition in which the muscle in the walls of at least one of the right and left sides of the heart deteriorates. By way of example, suppose the muscle in the walls of left side of the heart deteriorates. As a result, the left atrium and left ventricle become enlarged, and the heart muscle displays less contractility. This decreases cardiac output of blood through the circulatory system which, in turn, may result in an increased heart rate and less resting time between heartbeats. The heart consumes more energy and oxygen, and its condition typically worsens over a period of time.

In the above example, as the left side of the heart becomes enlarged, the intrinsic electrical heart signals that control heart rhythm may also be affected. Normally, such intrinsic signals originate in the sinoatrial (SA) node in the upper right atrium, traveling through electrical pathways in the atria and depolarizing the atrial heart tissue such that resulting contractions of the right and left atria are triggered. The intrinsic atrial heart signals are received by the atrioventricular (AV) node which, in turn, triggers a subsequent ventricular intrinsic heart signal that travels through specific electrical pathways in the ventricles and depolarizes the ventricular heart tissue such that resulting contractions of the right and left ventricles are triggered substantially simultaneously.

In the above example, where the left side of the heart has become enlarged due to congestive heart failure, however, the conduction system formed by the specific electrical pathways in the ventricle may be affected, as in the case of left bundle branch block (LBBB). As a result, ventricular intrinsic heart signals may travel through and depolarize the left side of the heart more slowly than in the right side of the heart. As a result, the left and right ventricles do not contract simultaneously, but rather, the left ventricle contracts after the right ventricle. This reduces the pumping efficiency of the heart. Moreover, in LBBB, for example, different regions within the left ventricle may not contract together in a coordinated fashion.

For these and other reasons, there is a need to provide cardiac rhythm management therapy that coordinates the timing of contractions of different sides of the heart, and/or alters the conduction of a depolarization through a single chamber of the heart to improve the efficiency of a contraction associated with that heart chamber.

SUMMARY

This document discusses a cardiac rhythm management system that selects one of multiple electrodes associated with a particular heart chamber. Subsequent contraction-evoking stimulation therapy is delivered from the selected electrode. Both methods and apparatuses are discussed.

In one embodiment, the electrode is selected based on a relative timing between detection of a same fiducial point of a cardiac depolarization at the multiple electrodes. The electrode that is last to detect the fiducial point is selected for subsequent delivery of contraction-evoking stimulations.

In another embodiment, a reference first chamber depolarization fiducial point is detected. A second chamber depolarization fiducial point is detected at each of multiple second chamber electrodes during the same cardiac cycle as the reference fiducial point. Time intervals are measured between the reference fiducial point and each of the second chamber fiducial points. The electrode corresponding to the longest such time interval is selected for subsequent delivery of contraction-evoking stimulations.

In a further embodiment, a first depolarization fiducial point is detected from the first heart chamber. During the same cardiac cycle, a second depolarization point is detected from a first electrode associated with the second heart chamber. A first time interval is measured between the first and second fiducial points. During a subsequent cardiac cycle, a third fiducial point, of the same nature as the first fiducial point, is detected from the first heart chamber. During the same cardiac cycle, a fourth fiducial point, of the same nature as the second fiducial point, is detected from a second electrode associated with the second heart chamber. A second time interval is measured between the third and fourth fiducial points. The electrode corresponding to the longer of the first and second time intervals is selected for subsequent delivery of contraction-evoking stimulations.

In yet a further embodiment, a reference fiducial point is detected, over one or more cardiac cycles, from one of a plurality of electrodes associated with a heart chamber. During the one or more cardiac cycles, corresponding fiducial points associated with heart depolarizations are detected at the electrodes, and time intervals are measured between the heart depolarization fiducial points and the respective reference fiducial points. The electrode associated with the longest time interval is used for subsequent delivery of stimulations. Other aspects of the present system and methods will become apparent upon reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments or examples. These embodiments may be combined, other embodiments may be utilized, and structural, logical and electrical changes may be made without departing from the spirit and scope of the present invention. The following detailed description is, therefore, not to be taken in a limiting sense, and the scope of the present invention is defined by the appended claims and their equivalents.

The present methods and apparatus are described with respect to implantable cardiac rhythm management (CRM) devices, such as pacemakers, cardioverter/defibrillators, pacer/defibrillators, and multi-chamber and/or multi-site (in a single or multiple heart chambers) cardiac resynchronization therapy (CRT) devices. Such CRT devices are included within CRM devices even though the CRT devices need not necessarily modulate heart rate. Such CRT devices may instead provide contraction-evoking stimulations that establish or modify the conduction path of propagating depolarizations to obtain more efficient pumping of the heart. Moreover, the present methods and apparatus also find application in other implantable medical devices, and in unimplanted (external) devices, including, but not limited to, external pacemakers, cardioverter/defibrillators, pacer/defibrillators, multi-chamber and/or multi-site CRT devices, monitors, programmers and recorders, whether such devices are used for providing a diagnostic, a therapy, or both.

Figure 1:
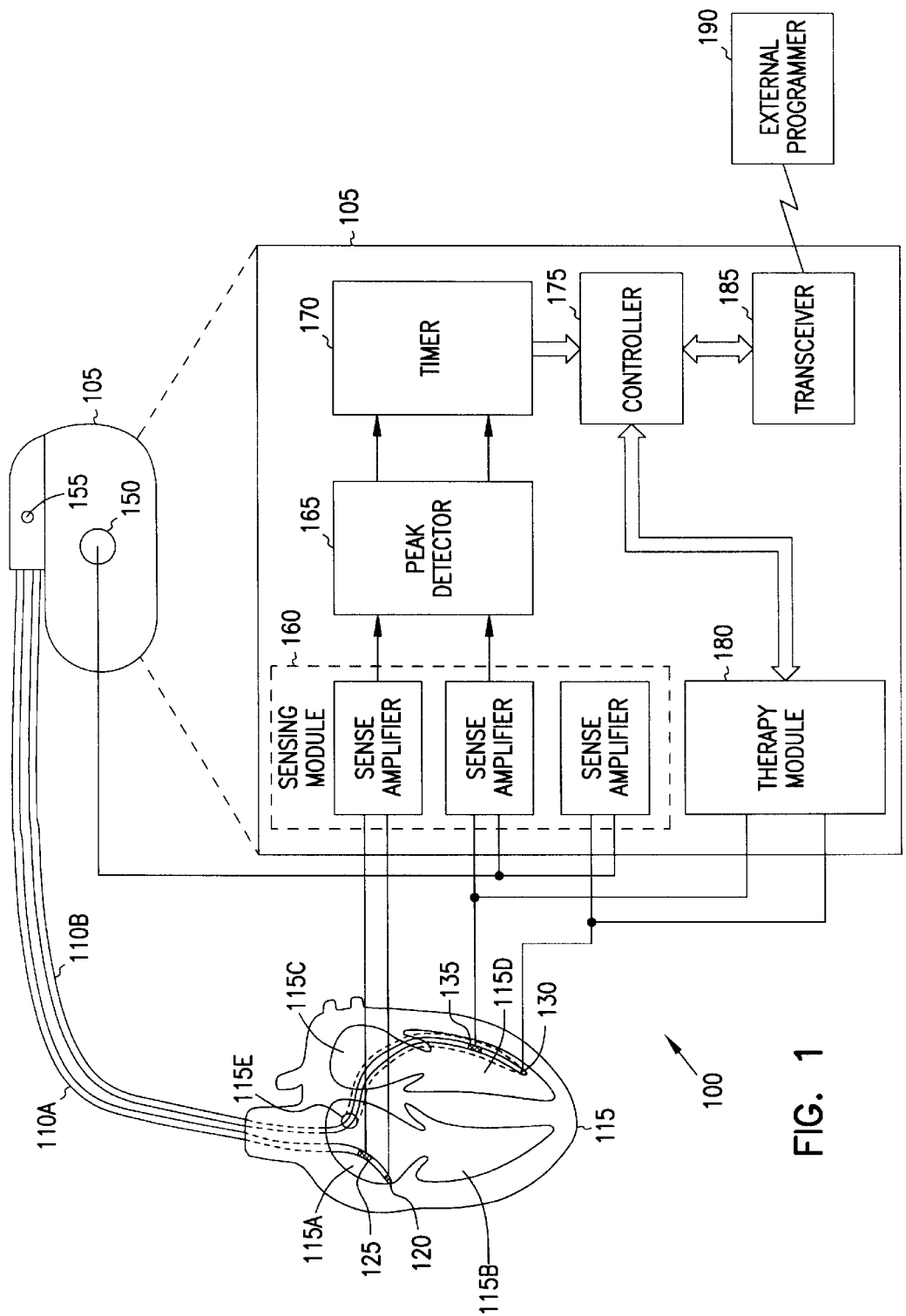
FIG. 1 is a schematic/block diagram illustrating generally, among other things, one embodiment of portions of a cardiac rhythm management system and an environment in which it is used.

FIG. 1 is a schematic/block diagram illustrating generally one embodiment of portions of the present cardiac rhythm management system 100 and an environment in which it is used. In this embodiment, system 100 includes, among other things, cardiac rhythm management device 105, which is coupled by leads 110A–B to heart 115. Heart 115 includes four chambers: right atrium 115A, right ventricle 115B, left atrium 115C, and left ventricle 115D. Heart 115 also includes a coronary sinus 115E, a vessel that extends from right atrium 115A toward the left ventricular free wall, and which, for the purpose of this document, is considered to include the great cardiac vein and/or tributary vessels.

In one embodiment, lead 110A includes an electrode associated with right atrium 115A, such as tip electrode 120 and/or ring electrode 125. The electrode is "associated" with the particular heart chamber by inserting it into that heart chamber, or by inserting it into a portion of the heart's vasculature that is close to that heart chamber, or by epicardially placing the electrode outside that heart chamber, or by any other technique of configuring and situating an electrode for sensing signals and/or providing therapy with respect to that heart chamber. Lead 110B, which is introduced into coronary sinus 115E and/or the great cardiac vein or one of its tributaries, includes one or a plurality of electrodes associated with left ventricle 115D, such as electrodes 130 and 135. Device 105 may also include other electrodes, such as housing electrode 150 and/or header electrode 155, which are useful for, among other things, unipolar sensing of heart signals or unipolar delivery of contraction-evoking stimulations in conjunction with one or more of the electrodes 120, 125, 130, and 135 associated with heart 115. Alternatively, bipolar sensing and/or therapy may be used between electrodes 120 and 125, between electrodes 130 and 135, or between one of electrodes 130 and 135 and another closely situated electrode.

Device 105 includes a sensing module 160, which is coupled to one or more of the electrodes for sensing electrical depolarizations corresponding to heart chamber contractions. Such electrical depolarizations of the heart tissue include atrial depolarizations, referred to as P-waves, and ventricular depolarizations, referred to as QRS complexes.

The QRS complex is a rapid sequence of several signal excursions away from a baseline in sequentially switching polarity, with the largest excursion referred to as an R-wave. Peak detector 165 is coupled to sensing module 160 for detecting the P-wave peak from right atrium 115A, obtained by bipolar sensing between electrodes 120 and 125 or by any other sensing technique. Peak detector 165 also senses the R-wave peak at a plurality of different sites associated with left ventricle, such as at each of electrodes 130 and 135. In one example, electrode 130 is located near the left ventricular apex and electrode 135 is located near the left ventricular base region, i.e., closer to the left atrium 115C. In another example, one of these two electrodes 130 and 135 (or an additional third electrode) is located in a middle portion ("midregion") of left ventricle 115D between the left ventricular apex and the left ventricular base region. In another example, electrodes 130 and 135 are located in a middle cardiac vein and closer to a septum region. The electrodes are located either on the free wall and/or the anterior wall of the ventricle. Sensing at electrodes 130 and 135 is either unipolar (e.g., the electrode 130 and/or 135 is sensed in combination with a relatively distant electrode, such as one or both of housing electrode 150 and/or header electrode 155) or bipolar (e.g., the electrode 130 and/or 135 is sensed in combination with another relatively close electrode, such as another electrode disposed on lead 110B and associated with left ventricle 115D, or another electrode disposed on lead 110A and associated with right atrium 115A). System 100 also includes a telemetry transceiver 185 in device 105, which is communicatively coupled to an external programmer 190.

Figure 2:
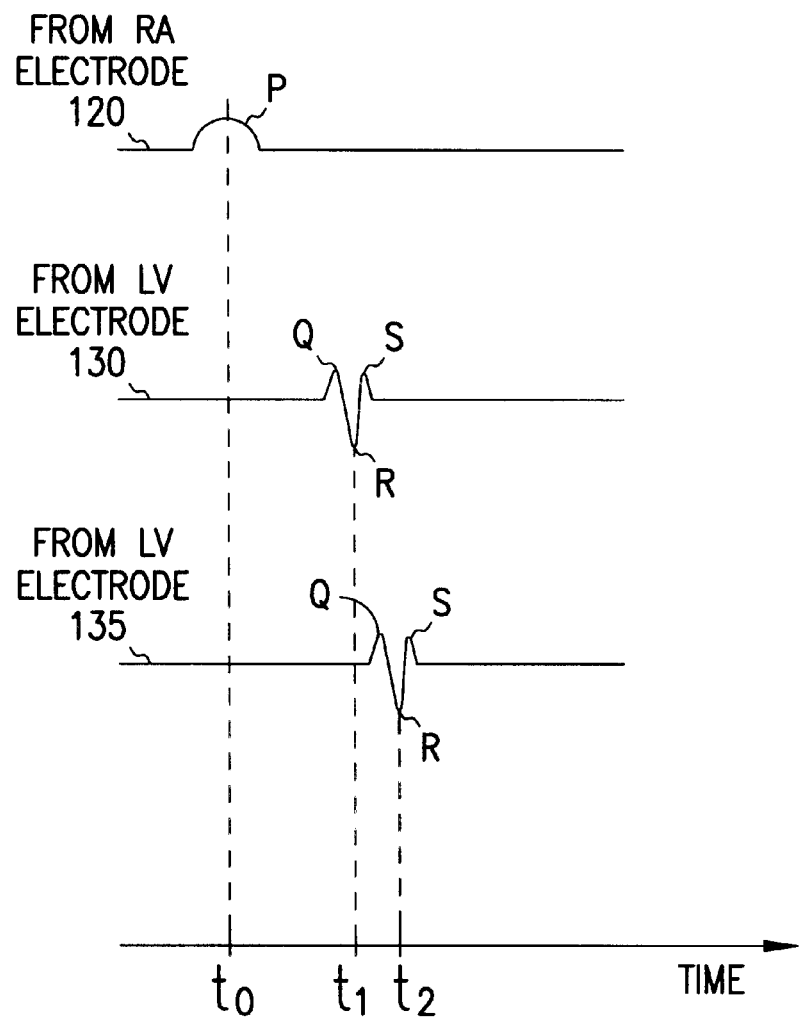
FIG. 2 is a graph illustrating generally, among other things, one technique of selecting between multiple electrodes associated with the same heart chamber.

FIG. 1, and the graph of FIG. 2, illustrates an embodiment in which timer 170 measures a first right atrium to left ventricle (RA–LV) time interval between the detection of an intrinsic P-wave at time $t_0$ at electrode 120 and the subsequent detection during the same cardiac cycle of an intrinsic R-wave peak at time $t_1$ at first left ventricular electrode 130. A cardiac cycle includes both an atrial and the resulting ventricular heart contraction, and may be measured between P-waves, between R-waves, or between any other fiducial points on a heart signal, where the fiducial point occurs once per cardiac cycle. Timer 170 also measures a second RA–LV time interval between the detection of the intrinsic P-wave at time $t_0$ at electrode 120 and the subsequent detection during the same cardiac cycle of an intrinsic R-wave peak at time $t_2$ at a second left ventricular electrode 135. Controller 175 is coupled to timer 170 to receive these first and second time intervals $(t_1-t_0)$ and $(t_2-t_0)$, respectively.

Based on a comparison between these time intervals, controller 175 selects one of electrodes 130 and 135 to which therapy module 180 is coupled for delivering subsequent contraction-evoking stimulation therapy to left ventricle 115D. In this example, controller 175 selects the one of electrodes 130 and 135 that corresponds to a longer detected time interval between the detection of the P-wave associated with the right atrium 115A and the detection of the R-wave associated with left ventricle 115D. Thus, if $(t_1-t_0)>(t_2-t_0)$, then electrode 130 is selected for delivering contraction-evoking stimulations. If $(t_1-t_0)<(t_2-t_0)$, then electrode 135 is selected for delivering contraction-evoking stimulations. If $(t_1-t_0)=(t_2-t_0)$, then, in one example, the electrode that is closest to the apex of heart 115 (e.g., electrode 130) is selected for delivering contraction-evoking stimulations. In a further example, a threshold time difference, $\Delta t$, is used for making the comparison. In this example, if $(t_1-t_0)>[(t_2-t_0)+\Delta t]$, then electrode 130 is selected for delivering stimulations. If $[(t_1-t_0)+\Delta t]<(t_2-t_0)$, then electrode 135 is selected for delivering stimulations. Otherwise, electrode 130, or other electrode closest to the apex of heart 115, is selected for delivering stimulations. In one example, $\Delta t$ is approximately between 0 milliseconds and 20 milliseconds inclusive, such as about 10 milliseconds. In a further example, an indication of which of electrodes 130 and 135 was selected is communicated from device 105 by transceiver 185 to external programmer 190 for display to a user.

In an alternate embodiment, the reference time $t_0$ is not used, but the relative times $t_1$ and $t_2$ are instead compared directly. If $t_1>t_2$, then electrode 130 is selected for delivering contraction-evoking stimulations, if $t_1<t_2$, then electrode 135 is selected for delivering contraction-evoking stimulations, if $t_1=t_2$, then electrode 130, or other electrode closest to the apex of heart 115, is selected for delivering contraction-evoking stimulations. In a further example, a threshold time difference, $\Delta t$, is used for making the comparison. For example, if $t_1>(t_2+\Delta t)$, then electrode 130 is selected for delivering stimulations, if $(t_1+\Delta t)<t_2$, then electrode 135 is selected for delivering stimulations, otherwise electrode 130, or other electrode closest to the apex of heart 115, is selected for delivering stimulations.

In another alternate embodiment, a reference time is used, but this reference time and the times $t_1$ and $t_2$ are measured during different cardiac cycles. During a first cardiac cycle, a P-wave is detected at electrode 120 at time $t_{0A}$ and an R-wave is detected at electrode 130 at time $t_1$, and a time interval $(t_1-t_{0A})$ is measured based on these detections. During a second cardiac cycle, another P-wave is detected at electrode 120 at time $t_{0B}$, and an R-wave is detected at electrode 135 at time $t_2$, and a time interval $t_2-t_{0B}$ is measured. The time intervals $(t_1-t_{0A})$ and $(t_2-t_{0B})$ are then compared, as discussed above, for selecting one of electrodes 130 and 135 for delivering stimulations.

In another alternate embodiment, a left atrial (LA) electrode is substituted for the right atrial electrode 120, and LA–LV time intervals are measured at each of the LV electrodes 130 and 135.

Figure 3:
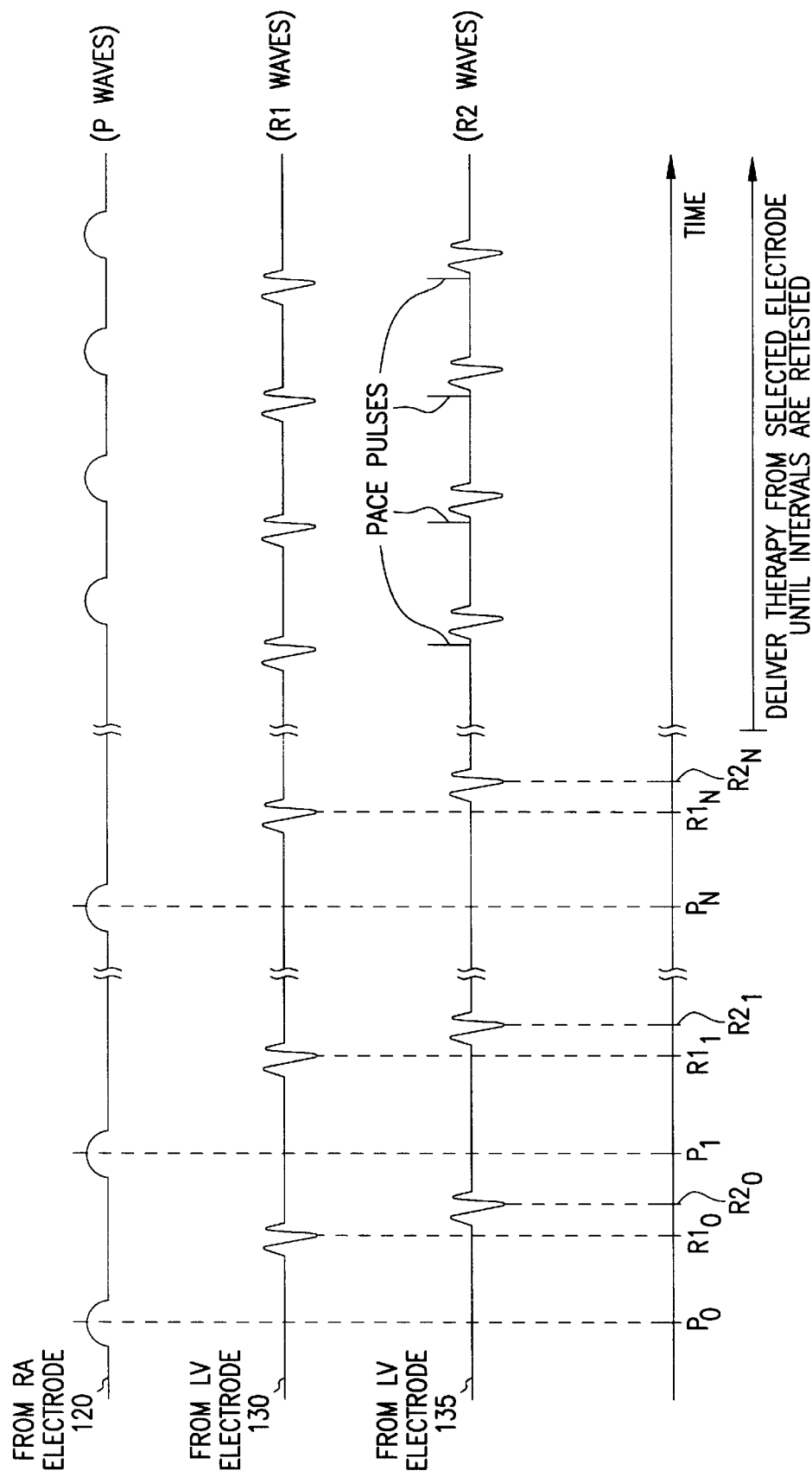
FIG. 3 is a graph illustrating generally, among other things, a technique of acquiring data over a plurality of cardiac cycles for selecting between multiple electrodes associated with the same heart chamber.

FIG. 3 is a graph illustrating generally another embodiment in which the P-R time intervals of interest are evaluated over a plurality of cardiac cycles for determining which of electrodes 130 and 135 to select for delivering therapy. In one example, a statistic, such as an average (or median or otherwise lowpass filtered value) over n consecutive or nonconsecutive intrinsic cardiac cycles, is computed for the P-R1 intervals detected between electrode 130 and electrode 120, and for the P-R2 intervals detected between electrode 135 and electrode 120. If the average P-R1 interval exceeds the average P-R2 interval, either absolutely or alternatively by a predetermined threshold time $\Delta t$, then electrode 130 is selected for delivering subsequent contraction-evoking stimuli. If the average P-R2 interval exceeds the average P-R1 interval, either absolutely or alternatively by a predetermined threshold time $\Delta t$, then electrode 135 is selected for delivering subsequent contraction-evoking stimuli. If the average P-R2 interval is equal to the average P-R1 interval, or alternatively the difference between these average intervals is less than or equal to the threshold time $\Delta t$, then the electrode closest to the apex of heart 115, such as electrode 130, is selected for delivering subsequent contraction-evoking stimuli.

In one embodiment, after such therapy is delivered over several cardiac cycles, then the therapy is occasionally or periodically (e.g., hourly, daily, monthly) turned off (either automatically or manually) for again performing one of the techniques described herein to determine which of electrodes 130 and 135 to provide therapy from during a subsequent time period.

Similar statistical techniques are used in an embodiment in which the selection of one of electrodes 130 and 135 for delivering contraction-evoking stimulations is based on the relative time of occurrence of depolarization fiducial points at electrodes 130 and 135, without using a reference point such as the P-wave. In one such example, the depolarization fiducial point is detected at both electrodes 130 and 135 over several consecutive or nonconsecutive cardiac cycles. If, on average, the depolarization fiducial point (e.g., R-wave peak) of a given cardiac cycle is detected at electrode 130 before it is detected at electrode 135, then electrode 135 is selected for delivering subsequent contraction-evoking stimulations, otherwise, electrode 130 is selected for delivering subsequent contraction-evoking stimulations. If, on average, the depolarization fiducial point (e.g., R-wave peak) of a given cardiac cycle is detected at electrode 130 at the same time that it is detected at electrode 135, then the electrode that is closest to the apex of heart 115, such as electrode 130, is selected. Moreover, such comparisons may use a threshold time such as discussed above.

Figure 4:
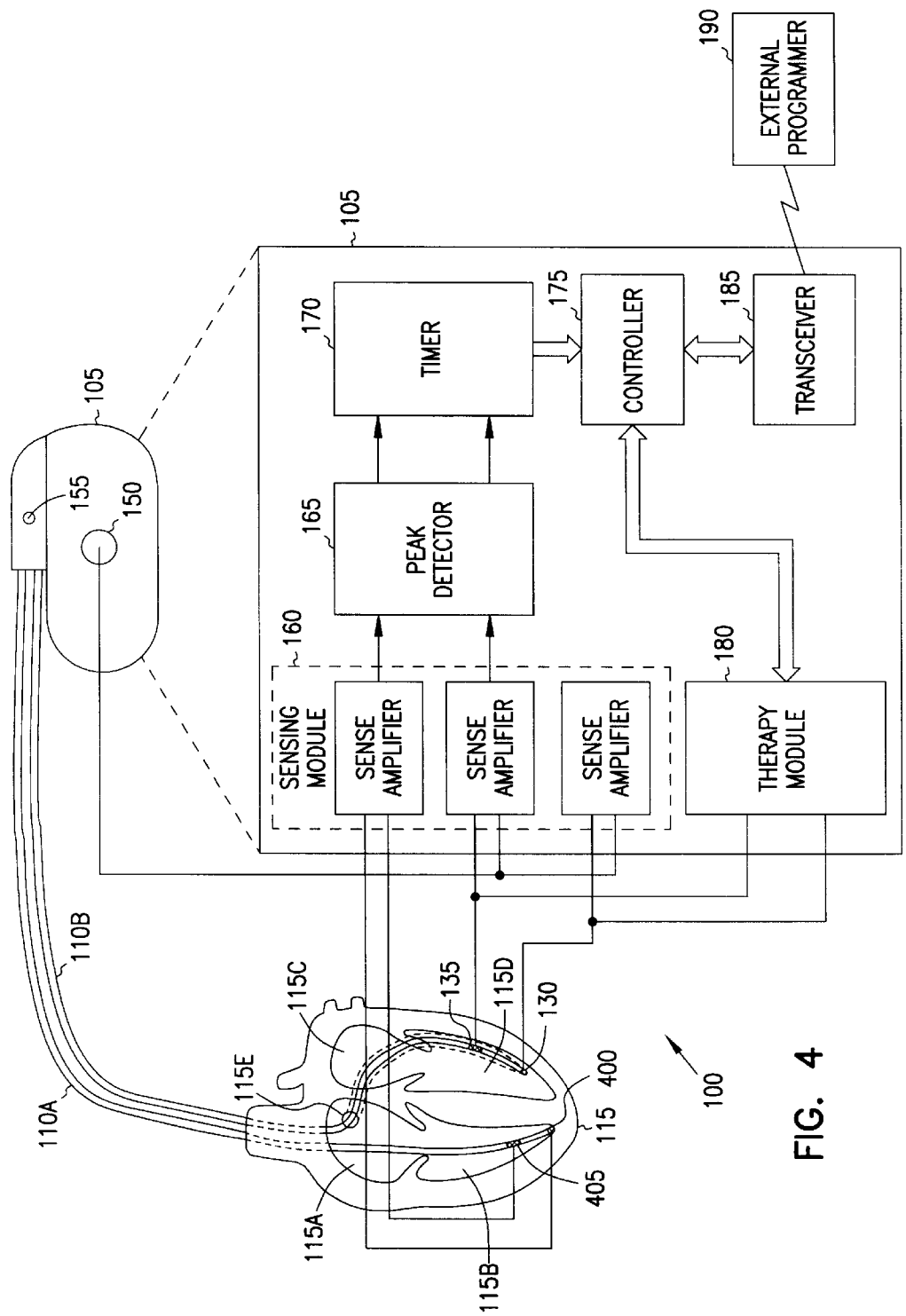
FIG. 4 is a schematic/block diagram illustrating generally, among other things, another embodiment of portions of a cardiac rhythm management system and an environment in which it is used.
Figure 5:
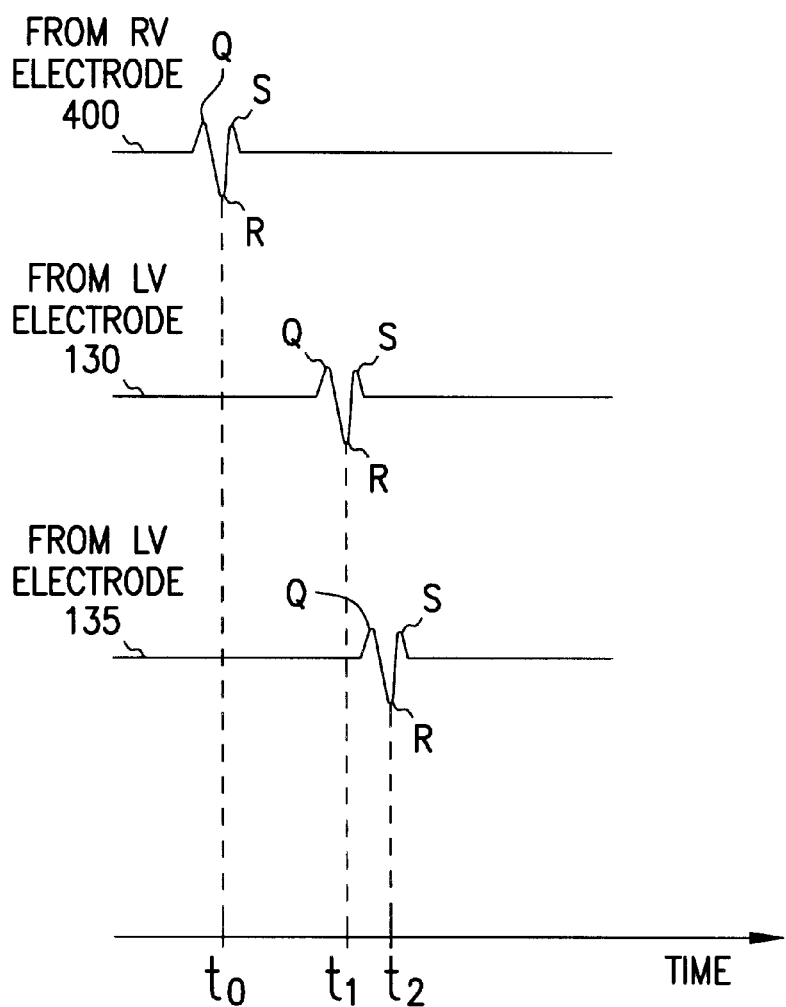
FIG. 5 is a graph illustrating generally, among other things, another technique of selecting between multiple electrodes associated with the same heart chamber.

FIG. 4 is a schematic/block diagram of one alternate embodiment including right ventricular electrodes, such as tip electrode 400 and ring electrode 405. FIG. 4, and the graph of FIG. 5, illustrates an embodiment in which timer 170 measures a first right ventricle to left ventricle (RV–LV) time interval between the detection of an intrinsic R-wave peak at time $t_0$ at right ventricular electrode 400 and the subsequent detection during the same cardiac cycle of an intrinsic R-wave peak at time $t_1$ at first left ventricular electrode 130. Timer 170 also measures a second RV–LV time interval between the detection of the intrinsic R-wave peak at time $t_0$ at right ventricular electrode 400 and the subsequent detection during the same cardiac cycle of an intrinsic R-wave peak at time $t_2$ at a second left ventricular electrode 135. Controller 175 is coupled to timer 170 to receive these first and second time intervals $(t_1-t_0)$ and $(t_2-t_0)$, respectively.

Based on a comparison between these time intervals, controller 175 selects one of electrodes 130 and 135 to which therapy module 180 is coupled for delivering subsequent contraction-evoking stimulation therapy to left ventricle 115D. In this example, controller 175 selects the one of electrodes 130 and 135 that corresponds to a longer detected RV–LV time interval between the detection of the R-wave associated with the right ventricle 115B and the detection of the R-wave associated with left ventricle 115D. Thus, if $(t_1-t_0)>(t_2-t_0)$, then electrode 130 is selected for delivering contraction-evoking stimulations. If $(t_1-t_0)<(t_2-t_0)$, then electrode 135 is selected for delivering contraction-evoking stimulations. If $(t_1-t_0)=(t_2-t_0)$, then the electrode closest to the heart apex, such as electrode 130, is selected for delivering contraction-evoking stimulations. As discussed above, in a further example, a threshold time difference, $\Delta t$, is used for making the comparison. Thus, if $(t_1-t_0)>[(t_2-t_0)+\Delta t]$, then electrode 130 is selected for delivering stimulations. If $[(t_1-t_0)+\Delta t]<(t_2-t_0)$, then electrode 135 is selected for delivering stimulations. Otherwise the electrode closest to the heart apex, such as electrode 130, is selected for delivering stimulations.

Figure 6:
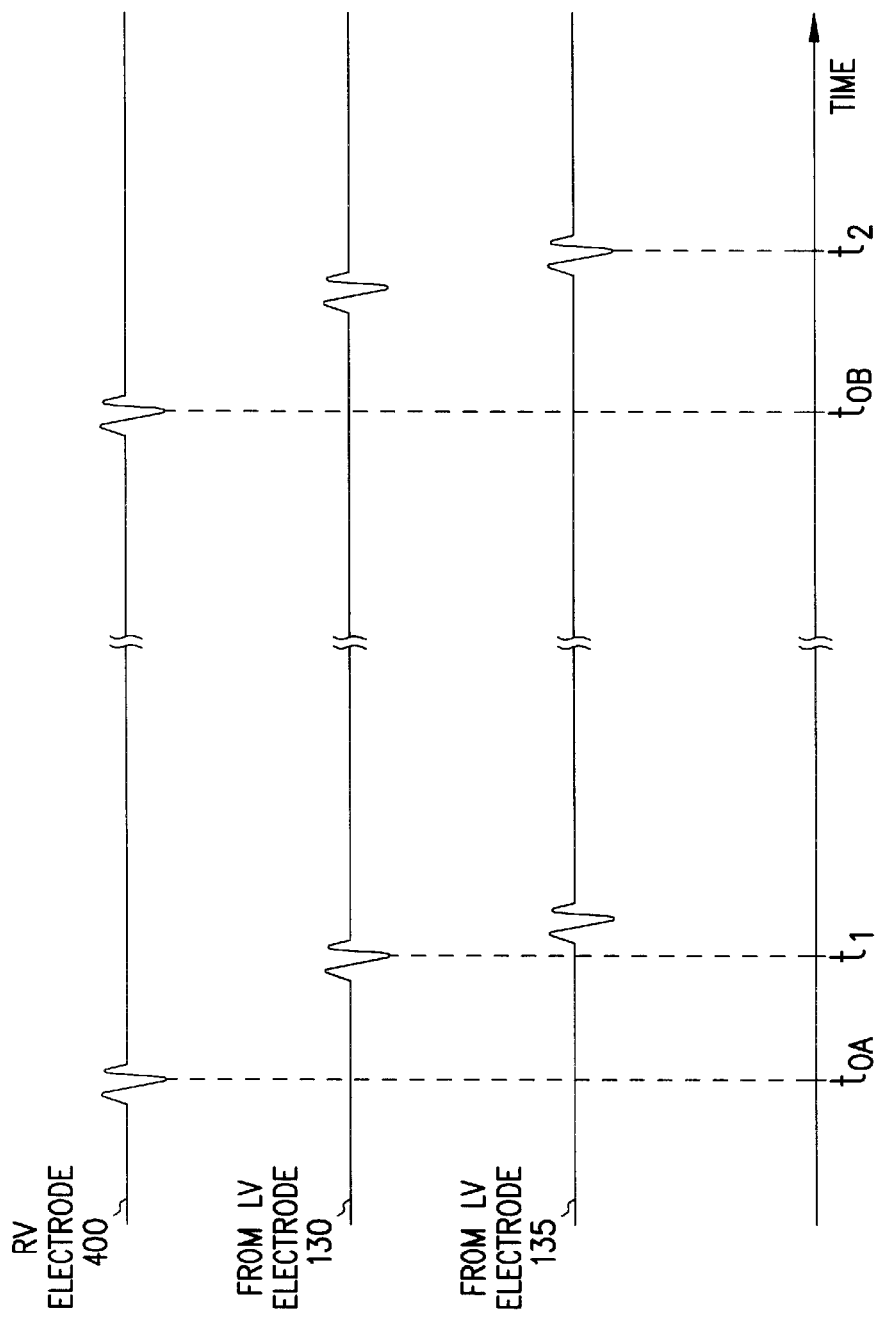
FIG. 6 is a graph illustrating generally, among other things, another technique of selecting between multiple electrodes associated with the same heart chamber, using time intervals obtained during different cardiac cycles.

As discussed above, the time intervals $(t_1-t_0)$ and $(t_2-t_0)$ need not be measured during the same cardiac cycle, as illustrated in the graph of FIG. 6. In the example of FIG. 6, a time interval $(t_1-t_{0A})$ is measured during a first cardiac cycle and a time interval $(t_2-t_{0B})$ is measured during a second (consecutive or nonconsecutive) cardiac cycle. In this example, if $(t_1-t_{0A})>(t_2-t_{0B})$, then electrode 130 is selected for delivering contraction-evoking stimulations. If $(t_1-t_{0A})<(t_2-t_{0B})$, then electrode 135 is selected for delivering contraction-evoking stimulations. If $(t_1-t_{0A})=(t_2-t_{0B})$, then the electrode that is closest to the apex of heart 115, such as electrode 130, is selected for delivering contraction-evoking stimulations. In a further example, as discussed above, a threshold time difference, $\Delta t$, is used for making the comparison. Thus, if $(t_1-t_{0A})>[(t_2-t_{0B})+\Delta t]$, then electrode 130 is selected for delivering stimulations. If $[(t_1-t_{0A})+\Delta t]<(t_2-t_{0B})$, then electrode 135 is selected for delivering stimulations. Otherwise, the electrode closest to the heart apex, such as electrode 130, is selected for delivering stimulations. By measuring the time intervals during different cardiac cycles, a single sense amplifier can be multiplexed between electrodes 130 and 135 for detecting the depolarization fiducial points. In certain embodiments, this advantageously allows for reduced circuitry. Although FIG. 6 illustrates an embodiment in which a right ventricular depolarization fiducial point is used as a reference point for measuring the time intervals, such techniques for measuring time intervals separately during different cardiac cycles is equally applicable to the other techniques discussed herein using other fiducial points.

Moreover, as discussed above, with respect to FIG. 3, in a further embodiment, data is acquired over a plurality of cardiac cycles, and a statistical comparison of RV–LV time intervals, with or without using $\Delta t$ for the comparison, is used to select the particular LV electrode for delivering contraction-evoking stimulations. In one embodiment, the subsequent contraction-evoking stimulation therapy is delivered without corresponding contraction-evoking stimulations delivered to right ventricle 115B. However, in another embodiment, each subsequent contraction-evoking stimulation therapy delivered by the selected one of left ventricular electrodes 130 and 135 is accompanied by a corresponding appropriately timed stimulation delivered by right ventricular electrode 400. This is referred to as biventricular cardiac resynchronization therapy. The stimulation delivered at the selected one of left ventricular electrodes 130 and 135 may be simultaneous to, or different from, the time of the corresponding stimulation delivered by right ventricular electrode 400.

Figure 7:
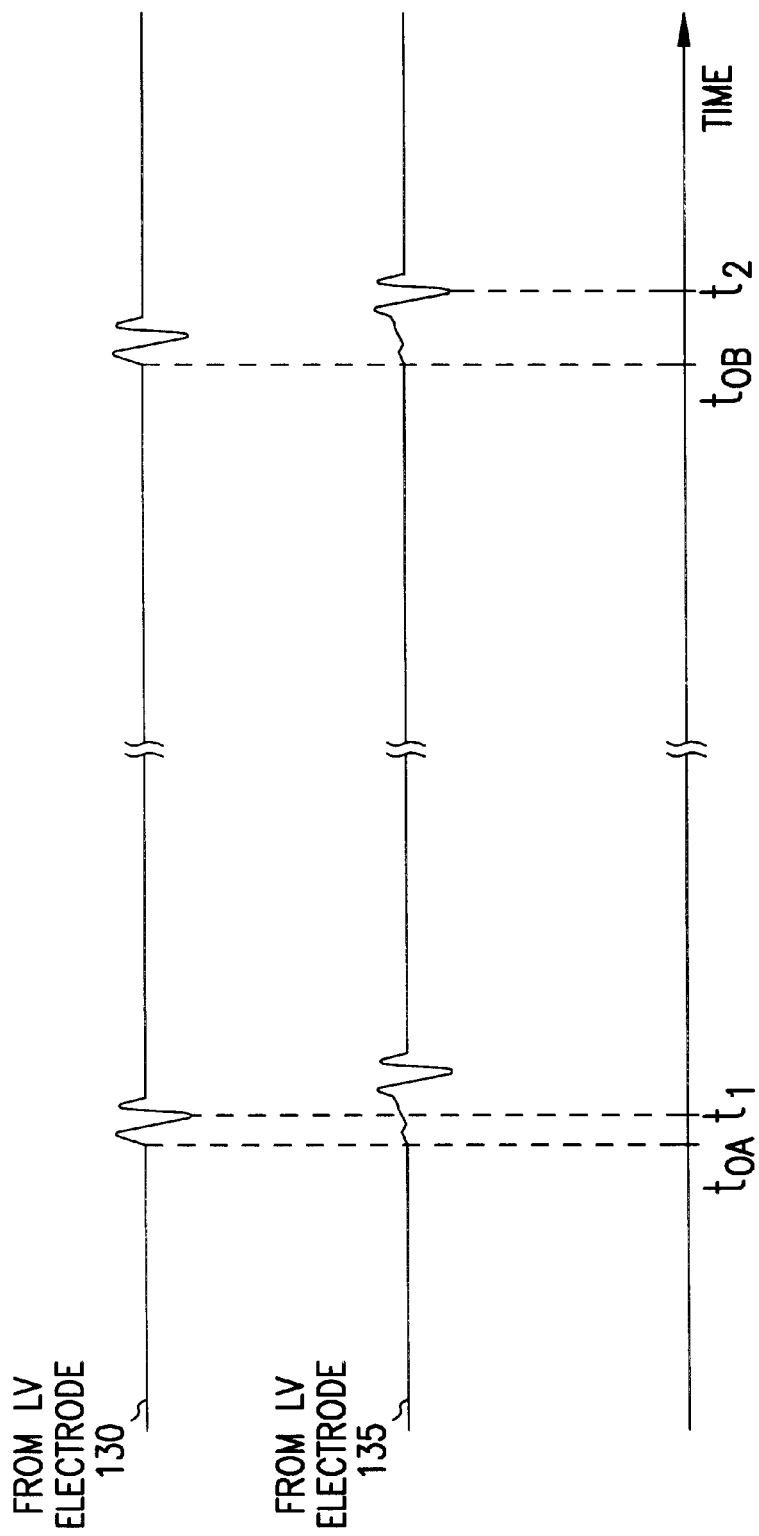
FIG. 7 is a graph example of selecting one of electrodes associated with the same heart chamber using time intervals measured from a reference fiducial point obtained from one of the same electrodes associated with that heart chamber.

FIG. 7 is a graph example of selecting one of the electrodes associated with the same heart chamber, such as left ventricle 115D, using time intervals measured from a reference fiducial point obtained from one of the same electrodes associated with that heart chamber. In this example, a reference fiducial point is obtained at time $t_{0A}$ by the first one of LV electrodes 130 and 135 to detect an onset of a QRS complex. This onset of the QRS complex, which is referred to as $Q^*$, serves as the reference fiducial point. One example of detecting $Q^*$ is discussed in Ding et al. U.S. Pat. No. 6,144,880, entitled "Cardiac Pacing Using Adjustable Atrio-Ventricular Delays," assigned to Cardiac Pacemakers, Inc., the entirety of which is incorporated herein by reference. The R-wave peak, or other fiducial point associated with a QRS complex, is detected at time $t_1$ at electrode 130. A first time difference $t_1-t_{0A}$ is measured. In this example, the same reference fiducial point is again detected, during a subsequent consecutive or nonconsecutive cardiac cycle, at time $t_{0B}$ by the first one of LV electrodes 130 and 135 to detect $Q^*$. The R-wave peak, or the other fiducial point similar to the fiducial point measured from electrode 130 at time $t_1$, is detected at time $t_2$ at electrode 135. A second time difference $t_2-t_{0B}$ is measured.

In this example, if $(t_1-t_{0A})>(t_2-t_{0B})$, then electrode 130 is selected for delivering contraction-evoking stimulations. If $(t_1-t_{0A})<(t_2-t_{0B})$, then electrode 135 is selected for delivering contraction-evoking stimulations. If $(t_1-t_{0A})=(t_2-t_{0B})$, then the electrode closest to the apex of heart 115, such as electrode 130, is selected for delivering contraction-evoking stimulations. In a further example, as discussed above, a threshold time difference, $\Delta t$, is used for making the comparison. Thus, if $(t_1-t_{0A})>[(t_2-t_{0B})+\Delta t]$, then electrode 130 is selected for delivering stimulations. If $[(t_1-t_{0A})+\Delta t]<(t_2-t_{0B})$, then electrode 135 is selected for delivering stimulations. Otherwise, the electrode closest to the heart apex, such as electrode 130, is selected for delivering stimulations. Although the example illustrated in FIG. 7 relates to using multiple cardiac cycles, it is understood that this technique could be carried out during a single cardiac cycle using a single reference point to substituted for the above reference points $t_{0A}$ and $t_{0B}$. Moreover, because Q* typically occurs substantially simultaneously at multiple electrodes associated with the same heart chamber, the Q* reference fiducial point can typically be detected from any one of the multiple electrodes associated with the same heart chamber.

FIGS. 1–6 illustrate that selecting the particular electrode, from a plurality of electrodes associated with left ventricle 115D, is in one embodiment based on the longer RA–LV measurement, and in another embodiment is based on the longer RV–LV measurement. In a further embodiment, selecting the particular electrode from a plurality of electrodes associated with the same ventricle is based on a time measurement from any selected reference fiducial point associated with any heart chamber to any other selected fiducial point associated with detection at the electrodes of one depolarization of that ventricle. One such example is illustrated in FIG. 7, in which a first left ventricular electrode detects a Q* fiducial point, then the second left ventricular electrode also detects the Q* fiducial points. Thus, the plurality of ventricular electrodes each detect the same type of fiducial point associated with the ventricular heart contraction. For example, if a first left ventricular electrode detects the R-wave peak, then the second left ventricular electrode also detects the R-wave peak. In another embodiment, if the first left ventricular electrode detects the point of maximum slope associated with a left ventricular R-wave, then the second left ventricular electrode also detects the point of maximum slope associated with the left ventricular R-wave. Stated differently, the left ventricular fiducial points are substantially similarly located on received heart depolarizations or, alternatively, may be located at different portions of the heart depolarization signal if the expected time interval between these different locations is known. FIGS. 1–6 particularly describe using P-wave and R-wave peaks as fiducial points, however, other examples of possible fiducial points include, among other things, a point of minimum slope on the detected heart signals. Moreover, as discussed above, the relative timing of the fiducial point detected at each same-chamber electrode can be compared directly, without using a reference fiducial point to establish corresponding time intervals as discussed above with respect to certain embodiments.

Moreover, in an alternative embodiment, for a heart 115 in which the electrical pathways cause the left ventricle to contract before the right ventricle, a left ventricular to right ventricular (LV–RV) delay is measured at a plurality of right ventricular electrodes, and subsequent contraction-evoking stimulations are delivered from that right ventricular electrode corresponding to the longest LV–RV delay. Thus, in a broader sense, a particular electrode from a plurality of electrodes associated with a first ventricle is selected for subsequent therapy delivery based on that electrode having a later detected depolarization than the other electrodes in the plurality of electrodes. In a further embodiment, system 100 not only selects between multiple electrodes associated with the same heart chamber, but also selects between right ventricle 115B and left ventricle 155D for delivering the contraction-evoking stimulations, such as described in Ding et al. U.S. patent application Ser. No. 09/738,407, assigned to Cardiac Pacemakers, Inc., the disclosure of which is incorporated herein by reference in its entirety.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method including:
    detecting a first fiducial point, associated with a first heart depolarization, at a first electrode associated with a first heart chamber;
    detecting the first fiducial point, associated with the first heart depolarization, at a second electrode associated with the first heart chamber;
    determining a time of the detection of the fist fiducial point at the first electrode and a time of the detection of the first fiducial point associated with the second electrode;
    selecting the first electrode if the first fiducial point is detected at the second electrode before the first fiducial point is detected at the first electrode, and selecting the second electrode if the first fiducial point is detected at the first electrode before the first fiducial point is detected at the second electrode; and
    delivering from the selected electrode a subsequent stimulation for evoking a contraction of the first heart chamber.

2. The method of claim 1, in which the first heart chamber is a ventricle, selected from a left ventricle and a right ventricle, and the first heart depolarization is a QRS complex associated with one contraction of the ventricle.

3. The method of claim 2, in which the first fiducial point is associated with a peak of an R-wave in the QRS complex.

4. The method of claim 2, further including disposing the first electrode at one of a base, midregion, and apex of a free wall of the ventricle, and disposing the second electrode at a different one of the base, midregion, and apex of the free wall of the ventricle.

5. The method of claim 1, in which selecting includes selecting the first electrode if, over a plurality of cardiac cycles, the first fiducial point is statistically detected at the second electrode before the first fiducial point is statistically detected at the first electrode, and selecting the second electrode if, over the plurality of cardiac cycles, the first fiducial point is statistically detected at the first electrode before the first fiducial point is statistically detected at the second electrode.

6. The method of claim 5, in which selecting further includes selecting one of the first and second electrodes located closer to a heart apex if the first fiducial point is statistically detected at both of the first and second electrodes at substantially the same time.

7. The method of claim 1, further including repeating the steps of claim 1 after a plurality of cardiac cycles.

8. The method of claim 1, in which selecting includes selecting one of the first and second electrodes that is closer to a heart apex if the first fiducial point is detected at both of the first and second electrodes at substantially the same time.

9. The method of claim 1, in which selecting includes selecting the first electrode if the first fiducial point is detected at the second electrode before, by at least a threshold time, the first fiducial point is detected at the first electrode, and selecting the second electrode if the first fiducial point is detected at the first electrode before, by at least the threshold time, the first fiducial point is detected at the second electrode.

10. The method of claim 1, in which determining the timing includes:

detecting at least one reference fiducial point;

measuring first and second time intervals between the at least one reference fiducial point and the first fiducial point detected at the respective first and second electrodes; and comparing the first and second time intervals.

11. A system including:

first and second electrodes, both configured to be associated with a first heart chamber;

a sensing circuit, coupled to the first and second electrodes, the sensing circuit detecting heart depolarizations associated with the first heart chamber, including detecting a first depolarization time at which a first depolarization of the first heart chamber is received at the first electrode, and detecting a second depolarization time at which the first depolarization of the first heart chamber is received at the second electrode;

a therapy circuit delivering stimulations for evoking heart contractions from at least one of the first and second electrodes; and a controller, coupled to the sensing circuit, the controller selecting the second electrode if the first depolarization time occurs before the second depolarization time, and selecting the first electrode if the second depolarization time occurs before the first depolarization time, the controller coupling the therapy circuit to the selected one of the first and second electrodes for delivering the stimulations.

12. The system of claim 11, in which the first and second electrodes are configured to be associated with a ventricle selected from a group consisting of a left ventricle and a right ventricle.

13. The system of claim 11, in which the sensing circuit provides, over a plurality of cardiac cycles, a plurality of first depolarization times and a plurality of second depolarization times, and the controller computes a first statistic associated with the plurality of first depolarization times and a second statistic associated with the plurality of second depolarization times, and the controller selects one of the first and second electrodes by comparing the first and second statistics, and the controller couples the therapy circuit to the selected one of the first and second electrodes for delivering the stimulations.

14. The system of claim 13, in which the controller selects the first electrode if the second depolarization times statistically occur before the first depolarization times and selects the second electrode if the first depolarization times statisically occur before the second depolarization times.

15. The system of claim 14, in which the controller selects one of the first and second electrodes that is located closer to a heart apex if the first and second depolarization times statisically occur at approximately the same time.

16. The system of claim 11, in which the controller selects the first electrode if the second depolarization occurs before the first depolarization by a predetermined threshold time, selects the second electrode if the first depolarization occurs before the second depolarization by the predetermined threshold time, and otherwise selects one of the first and second electrodes located closer to a heart apex.

17. The system of claim 11, in which after the therapy circuit delivers stimulations from the selected one of the first and second electrodes over a plurality of cardiac cycles, the controller again selects one of the first and second electrodes for then coupling the therapy circuit to the selected one of the first and second electrodes for delivering the stimulations.

18. The system of claim 11, further including a remote programmer communicatively coupled to the controller, the controller including an indication of which of the first and second electrodes is selected for delivering the stimulations, and the programmer capable of receiving the indication from the controller.

* * * * *

UNITED STATES PATENT AND TRADEMARK OFFICE
CERTIFICATE OF CORRECTION

PATENT NO. : 6,704,598 B2
DATED : March 9, 2004
INVENTOR(S) : Ding et al.

It is certified that error appears in the above-identified patent and that said Letters Patent is hereby corrected as shown below:

Title page,
Item [56], References Cited, OTHER PUBLICATIONS, delete "Sever" and insert -- Severe --, therefor.

Column 10,
Line 32, delete "fist" and insert -- first --, therefor.

Column 12,
Lines 20-21, delete "statisically" and insert -- statistically --, therefor.
Line 26, delete "statisically" and insert -- statistically --, therefor.

Signed and Sealed this

Eighteenth Day of May, 2004

JON W. DUDAS
*Acting Director of the United States Patent and Trademark Office*